United States Patent [19]
Schiller

[11] Patent Number: 5,811,400
[45] Date of Patent: Sep. 22, 1998

[54] PEPTIDE DERIVATIVES WITH δ OPIOID RECEPTOR ANTAGONIST OR MIXED μ AGONIST/δ ANTAGONIST EFFECTS

[75] Inventor: Peter Schiller, Montreal, Canada

[73] Assignee: Astra AB, Sweden

[21] Appl. No.: 532,688

[22] PCT Filed: Aug. 10, 1995

[86] PCT No.: PCT/SE95/00918

§ 371 Date: Oct. 6, 1995

§ 102(e) Date: Oct. 6, 1995

[87] PCT Pub. No.: WO96/06855

PCT Pub. Date: Mar. 7, 1996

[30] Foreign Application Priority Data

Aug. 30, 1994 [SE] Sweden .................................. 9402880

[51] Int. Cl.$^6$ .................................................. A61K 38/05
[52] U.S. Cl. ............................. 514/19; 562/444; 562/445
[58] Field of Search .............................. 514/19; 562/445, 562/444

[56] References Cited

FOREIGN PATENT DOCUMENTS

WO 94/15959  7/1994  WIPO.

OTHER PUBLICATIONS

Portoghese et al., "Application of the Message–Address Concept in the Design of Highly Potent and Selective Non–Peptide δ Opioid Receptor Antagonists," *J. Med. Chem.* 31:281–282, Letters to the Editor (1988).

Schiller et al., "Differential Stereochemical Requirements of μ vs. δ Opioid Receptors for Ligand Binding and Signal Transduction: Development of a Class of Potent and Highly δ–Selective Peptide Antagonists," *Proc. Natl. Acad. Sci. USA* 89:11871–11875 (1992).

Schiller et al.,"A New Class of Potent and Highly Selective δ Opioid Receptor Peptide Antagonists Without μ Antagonist Properties," *FASEB J* 6:A1575, Abstract No. 3699 (1992).

Schmidt et al., "Cyclic β–Casomorphin Analogues with Mixed μ Agonist/δ Antagonist Properties: Synthesis, Pharmacological Characterization, and Conformational Aspects," *J. Med. Chem.* 37:1136–1144 (1994).

Abdelhamid et al., "Selective Blockage of Delta Opioid Receptors Prevents the Development of Morphine Tolerance and Dependence in Mice," *J. Pharmacol. Exp. Ther.* 258:299–303 (1991).

Cotton et al., "ICI 174864: A Highly Selective Antagonist for the Opioid δ–Receptor," *Eur. J. Pharmacol.* 97:331–332 (1984).

Portoghese, "An Approach to the Design of Receptor–Type–Selective Non–Peptide Antagonists of Peptidergic Receptors: δ Opioid Antagonists," *J. Med. Chem.* 34:1757–1762 (1991).

*Primary Examiner*—Cecilia J. Tsang
*Assistant Examiner*—David Lukton
*Attorney, Agent, or Firm*—Michael A. Sanzo; Vinson & Elkins

[57] ABSTRACT

Compounds of the formula I

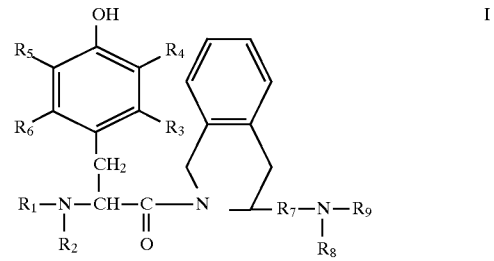

as well as methods for their preparation, their pharmaceutical preparations and their use in therapy, especially as analgesics and as immunosuppressive agents.

13 Claims, No Drawings

PEPTIDE DERIVATIVES WITH δ OPIOID RECEPTOR ANTAGONIST OR MIXED μ AGONIST/δ ANTAGONIST EFFECTS

THE FIELD OF THE INVENTION

This invention is related to a novel class of opioid peptide analogs that are δ opioid receptor antagonists or mixed μ agonist/δ antagonists as well as to their synthesis and their use as analgesics and immunosuppressive compounds.

BACKGROUND AND PRIOR ART

A known nonpeptide δ opioid antagonist is naltrindole, which is described by P. S Portoghese, et al J. Med. Chem. 31, 281–282 (1988). However, naltrindole has also quite high μ opioid receptor affinity ($K_i^\mu$=12 nM) in the receptor binding assay and, unlike the compounds according to the present invention, has potent μ antagonist properties ($K_e$=29 nM) in the guinea pig ileum (GPI) assay, cf P. S. Portoghese, J. Med. Chem. 34, 1757–1762 (1991).

Another known δ-antagonist is the enkephalin analog N,N-diallyl-Tyr-Aib-Aib-Phe-Leu-OH (ICI 174864) described by R. Cotton, et al. in Eur. J. Pharmacol. 97, 331–332 (1984). In comparison with some of the antagonists described in this patent application, ICI 174864 has much lower δ antagonist potency in the MVD assay (200 times less potent).

Peptides containing the H-Tyr-Tic-Aaa sequence (Tic=1,2,3,4-tetra-hydro-isoquinoline-3-carboxylic acid, Aaa=aromatic amino acid residue) at the N-terminus and which are very potent and highly selective δ antagonists have recently been disclosed by P. W. Schiller et al. in FASEB J, 6 (No. 4), A1575 (1992), at the International Narcotics Research Conference (INRC) Meetings in Keystone, Colo., Jun. 24–29 (1992) and in Skövde, Sweden, Jul. 10–15 (1993), at the 2nd Japan Symposium on Peptide Chemistry, Shizuoka, Japan, Nov. 9–13 (1992), at the 22nd European Peptide Symposium Interlaken, Switzerland, Sep. 9–13 (1992), in Proc. Natl. Acad. Sci. USA 89 11871–11875 (1992), and in J. Med. Chem. 36 3182–3187 (1993).

Peptides structurally related to TIPP that are mixed μ agonist/δ antagonists have recently been disclosed by P. W. Schiller et al. in Proc. Natl. Acad. Sci. USA 89, 11871–11875 (1992) and at the International Narcotics Research Conference (INRC) Meeting in North Falmouth, Mass., USA, Jul. 16–21 (1994). Cyclic β-casomorphin analogs with mixed μ agonist/δ antagonist properties have recently been disclosed by R. Schmidt et al. in J. Med. Chem. 37, 1136–1144 (1994). On the basis of results obtained by E. E. Abdelhamid et al., J. Pharmacol. Exp. Ther. 258, 299–303 (1991), mixed μ agonist/δ antagonists are of interest because they are expected to be analgesics with low propensity to produce tolerance and dependence.

The problem underlying the present invention was to find new dipeptide derivatives with δ antagonist or mixed μ agonist/δ antagonist properties that have a low molecular weight and are highly lipophilic. These properties should facilitate passage across the blood-brain barrier.

THE INVENTION

It has now been found that certain novel derivatives of the dipeptide H-Tyr-Tic-OH, as defined by the following formula I, have
high potency as δ antagonists
mixed μ agonist/δ antagonist properties
total lack of μ antagonist properties The novel compounds according to the present invention have the general formula I

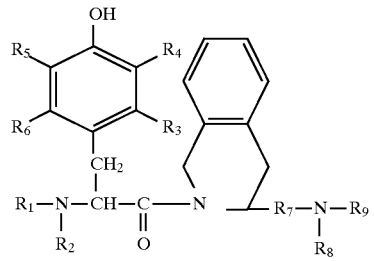

wherein
$R_1$ is H; $CH_3(CH_2)_n$—wherein n=0–12;

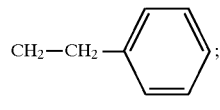

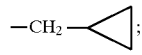

—$CH_2$—$CH$=$CH_2$; or argininyl;
$R_2$ is H; $CH_3(CH_2)_n$—wherein n=0–12;

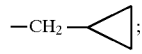

or
—$CH_2CH$=$CH_2$;
$R_3$, $R_4$, $R_5$, $R_6$ are all H; or
$R_4$ and $R_5$ are both H and $R_3$ and $R_6$ are both $C_1$–$C_6$ alkyl; or
$R_3$, $R_5$, $R_6$ are all H and $R_4$ is F, Cl, Br, OH, $NH_2$ or $NO_2$;
$R_7$ is carbonyl or $CH_2$;
$R_8$ is H or $C_1$–$C_{12}$ alkyl, or aralkyl wherein alkyl is $C_1$–$C_{12}$ alkyl;
$R_9$ is a linear or branched $C_1$–$C_{12}$ alkyl or aralkyl wherein alkyl is $C_1$–$C_{12}$ alkyl, or
$C_1$–$C_{12}$ alkyl linked to a heterocyclic moiety.
Illustrative examples of $R_9$ are

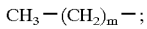

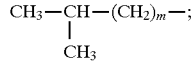

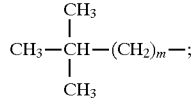

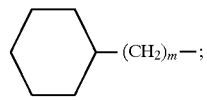

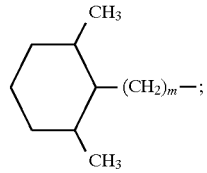

-continued

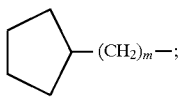

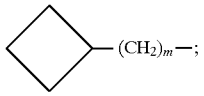

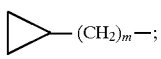

adamantyl—(CH$_2$)$_m$—;

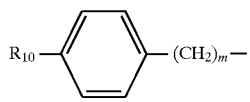

wherein

R$_{10}$ is H, F, Cl, Br, I, OH, NH$_2$, NO$_2$, CH$_3$ or phenyl;

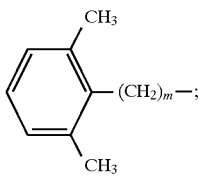

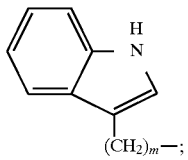

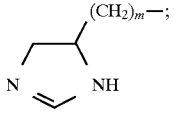

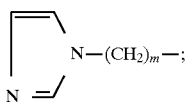

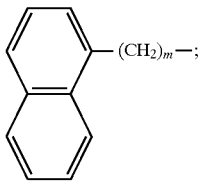

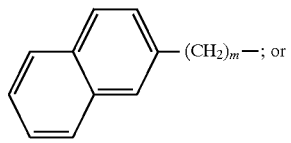

-continued

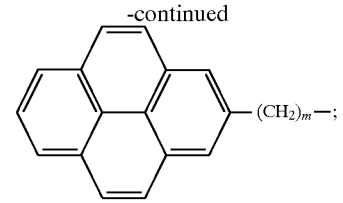

wherein m is 1–20 in all given examples of the R$_9$ definition.

Preferred compounds of the invention are those compounds wherein
R$_1$ is selected from H or CH$_3$;
R$_2$ is selected from H or CH$_3$;
R$_3$ is selected from H or CH$_3$;
R$_4$ is H;
R$_5$ is H;
R$_6$ is selected from H or CH$_3$;
R$_7$ is selected from carbonyl or CH$_2$;
R$_8$ is selected from H or CH$_3$; and
R$_9$ is selected from

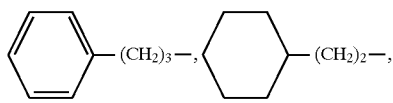

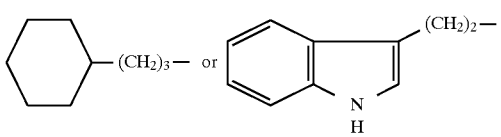

Especially preferred compounds of the invention are those, wherein R$_4$ and R$_5$ are H and R3 and R$_6$ are both methyl groups.

The best mode of carrying out the invention known at present is to use the compounds of Examples 4,14 and 18.

Synthesis

Most Boc-amino acid derivatives used in the peptide syntheses are commercially available. 2',6'-dimethyltyrosine (Dmt) was prepared as described by J. H. Dygos et al. Synthesis, No. 8 (August) pp. 741–743 (1992).

All dipeptide derivatives were prepared by solution synthesis by first coupling the C-terminal amine substituent to the carboxylic acid function of Boc-Tic-OH (mixed anhydride method), subsequent deprotection with acid, preferably an inorganic acid, especially preferred TFA, coupling of the Boc-protected N-terminal tyrosine or tyrosine analog (mixed anhydride method) and final deprotection with acid. The preferred acid system for Boc-deprotection is aqueous 95% TFA containing anisole (3%).

Compounds containing a reduced amide bond ($\Psi$[CH$_2$—NH]) between the Tic residue and the C-terminal substituent were obtained by first preparing Boc-Tic-3-(N-methoxy-N-methylamide) which was then deprotected with acid, TFA being especially preferred. The resulting product was coupled to the Boc-protected tyrosine or tyrosine analog (mixed anhydride method) and the dipeptide aldehyde was then obtained by reduction with lithium aluminium hydride. Subsequent reaction with the amine component, followed by treatment with sodium cyanoborohydride and final deprotection with TFA yielded the desired product.

The HPLC system GOLD (Beckman) consisting of the programmable solvent module 126 and the diode array detector module 168 was used for the purification and the purity control of the peptides. Reversed-phase HPLC was performed using a gradient made from two solvents: (A)

0.1% TFA in water and (B) 0.1% TFA in acetonitrile. For preparative runs a Vidac 218TP1022 column (250×22 mm) was used with a linear gradient of 15–40% B over a period of 45 min at a flow rate of 13 ml/min, absorptions being measured at both 216 nm and 280 nm. The same gradient was used for analytical runs on a Vidac 218TP 0046 column (250×4.6 mm) over a period of 30 min at a flow rate of 1.0 ml/min. Purity of peptides was also established by TLC on precoated silica gel plates 60F-254 (E. Merck, Darmstadt, FRG) in the following solvent systems (all v/v):

(A) $CHCl_3$/MeOH/AcOH (85:10:5), (B) n-BuOH/ $H_2O$/AcOH (4:1:1) and (C) EtOAc/hexane (1:1). Peptides were visualized with UV and with the ninhydrin spray reagent. Molecular weights of the peptides were determined by FAB mass spectrometry on an MS-50 HMTCTA mass spectrometer interfaced with a DS-90 data system. Melting points were determined on an electrothermal melting point apparatus and are uncorrected.

DETAILED DESCRIPTION OF THE INVENTION

The invention will now be described in more detail by the following examples.

Peptide Synthesis—General methods

1) Mixed Anhydride Method

NMM (1 equiv.) was added to a stirred solution of 1 mmol of the Boc-protected amino acid in THF. The mixture was cooled to −15° C., treated with IBCF (1 equiv.) and was allowed to react for 3–4 min. Subsequently, the amino component (1 equiv.) was added. The reaction mixture was stirred for 30 min at −15° C. and was then allowed to reach room temperature. The solvent was then removed by vacuum evaporation and the residual oil was dissolved in 100 ml of EtOAc. The resulting solution was extracted consecutively with brine, 5% $KHSO_4$, brine, saturated $NaHCO_3$ and brine. The organic phase was dried ($MgSO_4$), filtered and evaporated to dryness. The resulting crude products were used for deprotection without prior purification.

2) Deprotection

The Boc-protected peptides were deprotected using aqueous 95% TFA containing thioanisole (3%) under stirring and cooling with ice. After evaporation in vacuo, the pure TFA salts of the peptides were obtained by crystallization from EtOH/ether or by HPLC purification.

EXAMPLE 1

A) Preparation of H-Tic-NH-$(CH_2)_3$—Ph (Compound 1)

Boc-Tic-OH (1.5 mmol) was coupled with $H_2N$—$(CH_2)_3$—$C_6H_5$ (3-phenyl-1-propylamine, 1.5 mmol) according to method 1. After deprotection compound 1 was obtained by crystallization from EtOH/ether in 95% yield.

FAB-MS: $MH^+$=295

TLC (silica): Rf=0.40 (A), Rf=0.68 (B)

mp=148°–150° C.

B) Preparation of H-Tyr-Tic-NH-$(CH_2)_3$—Ph

Using the mixed anhydride method, Boc-Tyr(Boc)—OH (1 mmol) was coupled with the TFA salt of compound 1 (1 mmol) in the presence of NMM (1 equiv.). After deprotection the crude product was purified by HPLC. Compound 2 in pure form was obtained in 80% yield.

FAB-MS: $MH^+$=458

TLC (silica): Rf=0.29 (A), Rf=0.65 (B)

HPLC: K'=6.8.

The compounds of Examples 2–19 have been synthesized as described for Example 1 above.

EXAMPLE 20

A) Preparation of Boc-Tyr(Boc)-Tic-3-(N-methoxy-N-methylamide) (Compound 2)

Boc-Tic-3-(N-methoxy-N-methylamide), prepared as described by P. W. Schiller et al., in J. Med. Chem. 36 3182–3186 (1993), was deprotected using method 2) described above (95 % yield; TLC (silica): Rf=0.31 (A)). Coupling of Boc-Tyr(Boc)-OH was performed according to method 1) described above and the resulting crude product was purified by flash chromatography on silica gel with hexane/EtOAc (2:1) as eluent (48 % yield).

FAB-MS:$MH^+$584

TLC (silica): Rf=0.85 (A); Rf=0.28 (C).

B) Preparation of Boc-Tyr(Boc)-Tic-3-aldehyde (Compound 3)

580 mg (1 mmol) of compound 2 was dissolved in 10 ml of ice-cold EtOH and 100 mg (2 mmol) of lithium aluminium hydride was added under stirring. The reaction was carried out for 1 h at 0 ° C. 50 ml of ether followed by an ice-cold solution (50 ml) of 20% citric acid were then added and the mixture was vigorously stirred for 30 min. The organic layer was collected and the aqueous phase was extracted again with ether (50 ml). The combined ether extracts were washed with saturated $NaHCO_3$, brine, 10 % citric acid and $H_2O$, dried over $MgSO_4$, and evaporated in vacuo to yield a clear oil (50 % yield).

TLC (silica): Rf=0.49 (C).

C) Preparation of H-Tyr-TicΨ[CH—NH]$(CH_2)_3$—Ph

The aldehyde (Compound 3) (270 mg, 0.5 mmol) was dissolved in 10 ml of MeOH/AcOH (99:1) containing 3-phenylpropylamine (97 μl, 0.5 mmol). Sodium cyanoborohydride (38.2 mg, 0.6 mmol) was then added portionwise over a period of 45 min and the reaction was carried out for 15 h. At the end of the reaction saturated $NaHCO_3$ (50 ml) was added under stirring, followed by an addition of 100 ml EtOAc. The organic phase was collected, washed with water and dried over $MgSO_4$. After evaporation of the solvent, the obtained product was deprotected by using method 1) described above, and the crude target compound was purified by HPLC (yield=42%).

FAB-MS: MH=444

TLC (silica): Rf=0.24 (A); Rf=0.18 (B)

Examples of compounds prepared according to the invention are given below in Table 1.

TABLE 1

| Ex. | Compound | FAB-MS MH+ (molecular weight) |
|---|---|---|
| 1 | H—Tyr—Tic—NH—(CH$_2$)$_3$—C$_6$H$_5$ | 458 |
| 2 | H—Tyr—Tic—NH—(CH$_2$)$_4$—C$_6$H$_5$ | 472 |
| 3 | H—Tyr—Tic—NH—(CH$_2$)—C$_6$H$_5$ | 430 |
| 4 | H—Dmt—Tic—NH—(CH$_2$)$_3$—C$_6$H$_5$ | 486 |
| 5 | H—Tyr—Tic—NH—(CH$_2$)$_3$—N(imidazole) | 448 |
| 6 | H—Tyr—Tic—NH—(CH$_2$)$_3$—CH$_3$ | 396 |
| 7 | H—Tyr—Tic—NH—(CH$_2$)$_5$—CH$_3$ | 424 |
| 8 | H—Tyr—Tic—NH—(CH$_2$)$_9$—CH$_3$ | 468 |
| 9 | H—Tyr—Tic—NH—(CH$_2$)$_{11}$—CH$_3$ | 508 |
| 10 | H—Tyr—Tic—NH—(CH$_2$)$_3$—(2,6-dimethylphenyl) | 486 |
| 11 | H—Dmt—Tic-Ψ[CH$_2$—NH](CH$_2$)$_3$—N(imidazole) | 472 |
| 12 | H—Tyr—Tic—NH—(CH$_2$)$_3$—cyclohexyl | 464 |
| 13 | H—Tyr—Tic—NH—(CH$_2$)$_2$—cyclohexyl | 450 |
| 14 | H—Dmt—Tic—NH—(CH$_2$)$_2$—cyclohexyl | 478 |
| 15 | H—Tyr—Tic—NH—(CH$_2$)$_2$—C$_6$H$_4$—F | 490 |
| 16 | H—Tyr—Tic—NH—(CH$_2$)$_2$—C$_6$H$_4$—Cl | 478 |
| 17 | H—Tyr—Tic—NH—(CH$_2$)$_2$—indolyl | 483 |
| 18 | H—Dmt—Tic—NH—(CH$_2$)$_2$—indolyl | 511 |
| 19 | H—Tyr—Tic—NH—(CH$_2$)$_3$—naphthyl | 508 |
| 20 | H—Tyr—N(cyclic)—CH$_2$—NH—(CH$_2$)$_3$—C$_6$H$_5$ | 444 |

Pharmacological testing in vitro of δ opioid antagonists with a μ agonist component Biosassys based on inhibition of electrically evoked contractions of the mouse vas deferens (MVD) and of the guinea pig ileum (GPI) were performed. In the GPI assay the opioid effect is primarily mediated by μ opioid receptors, whereas in the MVD assay the inhibition of the contractions is mostly due to interaction with δ opioid receptors. Antagonist potencies in these assays are expressed as so-called $K_e$-values (H. W. Kosterlitz & A. J. Watt, Br. J. Pharmacol. 33 266–276 (1968)). Agonist potencies are expressed as IC50 values (concentration of the agonist that produces 50% inhibition of the electrically induced contractions).

Bioassays Using Isolated Organ Preparations

The GPI and MVD bioassays were carried out as reported in P. W. Schiller et al., Biochem. Biophys. Res. Commun 85, 1332–1338 (1978) and J. Di Maio et al., J. Med. Chem. 25, 1432–1438 (1982). A log dose-response curve was determined with [Leu$^5$]enkephalin as standard for each ileum and vas preparation, and IC50 values of the compounds being tested were normalized according to A. A Waterfield et al., Eur. J. Pharmacol. 58, 11–18 (1979). $K_e$ values for the δ opioid antagonists were determined from the ratio of IC50 values (DR) obtained in the presence and absence of a fixed antagonist concentration (a) ($K_e$=a/(DR-1)) H. W. Kosterlitz & A. J. Watt, Br. J. Pharmacol. 33 266–276 (1968). These determinations were made with the MVD assay, using two different δ-selective agonists (DPDPE and [D-Ala$^2$] deltorphin I).

Conclusion

Based on the results from the tests performed, the following conclusions could be made:

All compounds showed δ antagonist properties

All compounds showed no μ antagonist activity in the GPI assay at concentrations as high as 10 μM.

All compounds were either partial or full μ agonists in the GPI assay.

Compounds 4, 14 and 18 were a potent mixed μ agonist/δ antagonists.

Opioid receptor binding assays

μ and δ opioid receptor binding constants ($K_i^\mu$, $K_i^\delta$) of the compounds were determined by displacement of relatively selective μ and δ radioligands from binding sites in rat brain membrane preparations (calculated from the measured IC50 values on the basis of the equation by Cheng & Prusoff (Y. C. Cheng and W. H. Prusoff (Biochem. Pharmacol. 22 3099–3102 (1973)).

The ratio $K_i^\mu/K_i^\delta$ was a quantitative measure of the δ-versus μ receptor selectivity.

Opioid receptor binding studies

The μ-, δ- and κ-opioid receptor affinities of all new analogs were determined in binding assays based on displacement of μ-, δ-and κ-selective radioligands from rat brain membrane binding sites. In the case of κ-ligands guinea pig brain homogenates were used, since the relative proportion of κ-binding sites is higher in guinea pig brain than in rat brain. The experimental procedure being used in our laboratory represents a modified version of the binding assay described by Pasternak et al. (Mol. Pharmacol. 11, 340–351, (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris-HCl, pH 7.7). After centrifugation at 30,000 x g for 30 min at 4° C. the membranes were reconstituted in the original volume of standard buffer and incubated for 30 min at 37° C. (to realease bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [$^3$H]DAMGO, μ-selective, 0.7 nM; [$^3$H]DSLET, [$^3$H]DPDPE, or [$^3$H]TIPP, δ-selective, 1.0 nM; and [$^3$H] U69,563, κ-selective, 0.5 nM. The incubation was terminated by filtration through Whatman GF/B filters under vacuum at 4° C. Following two washings with 5 ml portions of ice-cold standard buffer the filters were transferred to scintillation vials and treated with 1 ml Protosol (New England Nuclear) for 30 min prior to the addition of 0.5 ml acetic acid and 10 ml Aquasol (New England Nuclear). After shaking for 30 min the vials were counted at an efficiency of 40–45%. All experiments were performed in duplicates and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of specific binding were obtained graphically from semilogarithmic plots. From the measured IC50-values, binding inhibition constants ($K_i$) were then calculated based on Cheng and Prusoff's equation (Biochem, Pharmcol. 22 3099–3102 (1973)). Ratios of the K.-values in the μ-, δ- and κ-representative binding assays are a measure of the receptor selectively of the compound under investigation (e.g. $K_i^\mu/K_i^\delta$ indicates the selectivity for δ-receptors versus μ-receptors). None of the compounds according to the claimed invention had significant affinity for κ-receptors.

Potential use

The δ antagonists with a weak partial μ agonist component may be used in combination with analgesics of the i agonist type (e.g. morphine) to prevent the development of tolerance and dependence, refer to the results of E. E. Abdelhamid et al., J. Pharmacol. Exp. Ther. 258, 299–303 (1991). The latter study also supports the conclusion that compounds with mixed μ agonist/δ antagonist properties are therapeutically useful as analgesics that do not produce tolerance and dependence. The dipeptide derivatives containing 2',6'-dimethyltyrosine (Dmt) in place of Tyr[1] described in the present patent application are potent mixed μ agonist/δ antagonists of relatively low molecular weight.

The δ antagonists with a weak partial μ agonist component described in the present patent application may also be therapeutically useful as immunosuppressive agents. Immunosuppressive effects of the δ antagonist naltrindole have been described by K. Arakawa et al. Transplantation Proc. 24, 696–697 (1992); Transplantation 53, 951–953 (1992).

Abbreviations

Aib=α-aminoisobutyric acid
Boc=tert-butoxycarbonyl
DAMGO=H-Tyr-D-Ala-Gly-Phe(N$^\alpha$Me)-Gly-ol
Dmt=2',6'-dimethyltyrosine

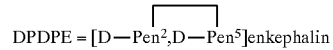

DSLET=H-Tyr-D-Ser-Gly-Phe-Leu-Thr-OH
FAB-MS=fast atom bombardment mass spectrometry
GPI=guinea pig ileum
HPLC=high performance liquid chromatography
IBCF=isobutylchloroformate
MVD=mouse vas deferens
NMM=N-methylmorpholine
TFA=trifluoroacetic acid
THF=tetrahydrofuran
Tic=1,2,3,4-tetrahydroisoquinoline-3-carboxylic acid
TIPP=H-Tyr-Tic-Phe-Phe-OH
TLC=thin layer chromatography
U69,593=(5α, 7α, 8β)-(−)-N-methyl-[7-(1-pyrrolidinyl)-1-oxaspiro[4,5]dec-8-yl]benzeneacetamide

I claim:

1. A compound of the formula

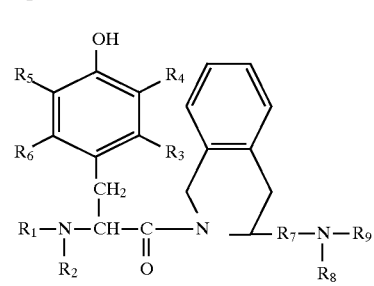

wherein $R_1$ is H; $CH_3(CH_2)_n$—wherein n=0–12;

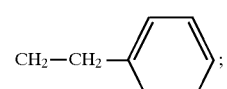

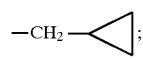

—$CH_2$—CH=$CH_2$; or argininyl:

$R_2$ is H; $CH_3(CH_2)_n$—wherein n 0–12;

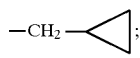

or

—$CH_2$—CH=$CH_2$;

$R_3$, $R_4$, $R_5$, $R_6$ are all H; or $R_4$ and $R_5$ are both H and $R_3$ and $R_6$ are both $C_1$–$C_6$ alkyl; or $R_3$, $R_5$, $R_6$ are all H and $R_4$ is F, Cl, Br, OH, NH2 or $NO_2$;

$R_7$ is carbonyl or $CH_2$;

$R_8$ is H or $C_1$–$C_{12}$ alkyl, or aralkyl wherein alkyl is $C_1$–$C_{12}$ alkyl;

$R_9$ is a linear or branched $C_1$–$C_{12}$ alkyl or aralkyl wherein alkyl is $C_1$–$C_{12}$ alkyl, or a $C_1$–$C_{12}$ alkyl linked to a heterocyclic moiety or a cyclohexylalkyl.

2. A compound of the formula I according to claim 1, wherein $R_1$ is selected from H or $CH_3$;

$R_2$ is selected from H or $CH_3$;

$R_3$ is selected from H or $CH_3$;

$R_4$ is H;

$R_5$ is H;

$R_6$ is selected from H or $CH_3$;

$R_7$ is selected from carbonyl or $CH_2$;

$R_8$ is selected from H or $CH_3$; and $R_9$ is selected from

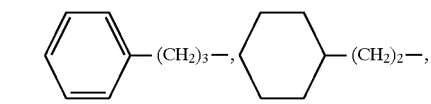

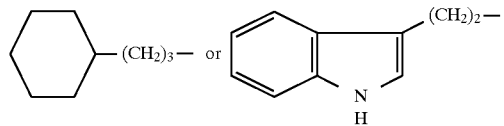

3. A compound according to formula I of claim 1, wherein $R_4$ and $R_5$ are H and $R_3$ and $R_6$ are both methyl groups.

4). A compound selected from the group consisting of:

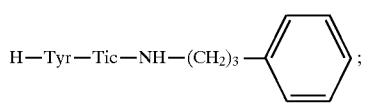

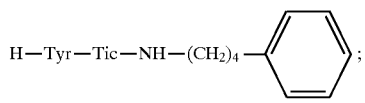

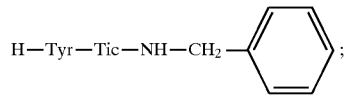

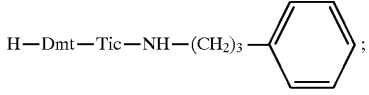

-continued

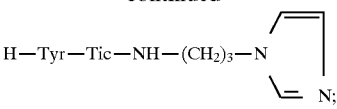

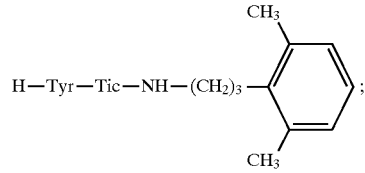

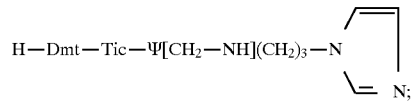

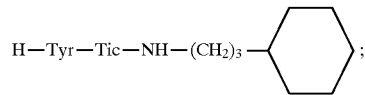

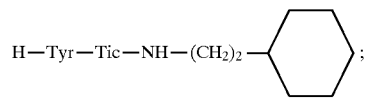

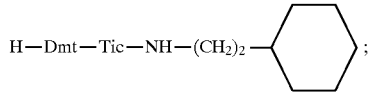

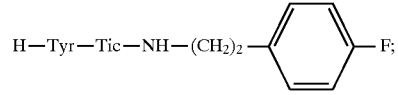

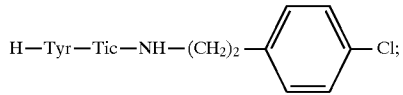

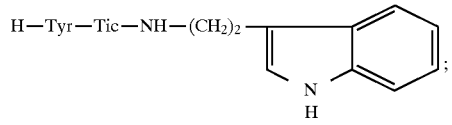

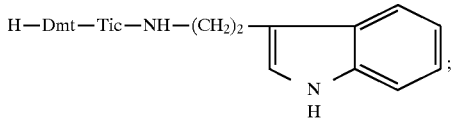

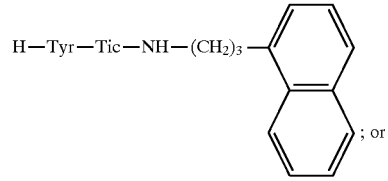

-continued

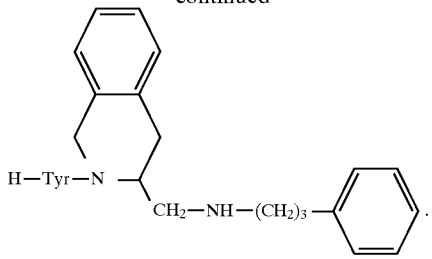

5. A compound according to formula I of claim 1, wherein said compound is selected from the group consisting of:

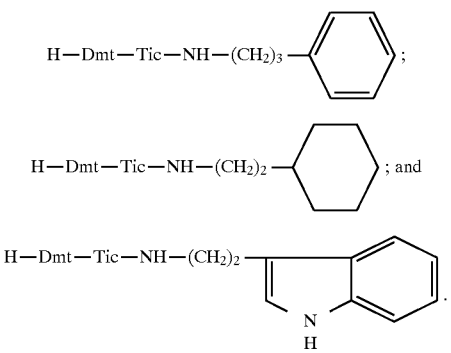

6. A compound according to formula I of claim 1 wherein said compound has an analgesic effect when administered to a patient.

7. A compound according to formula I of claim 1 wherein said compound has an immunosuppressive effect when administered to a patient.

8. A pharmaceutical preparation comprising a compound of formula I according to claim 1 as an active ingredient, optionally together with one or more pharmaceutically acceptable carriers.

9. A method for treating a patient experiencing pain, said method comprising administering a compound of formula I according to claim 1, wherein said compound is administered at a dose effective to reduce or eliminate said pain.

10. A method for producing an immunosuppressive effect in a patient, said method comprising administering a compound of formula I according to claim 1, wherein said compound is administered at a dose effective to induce immunosuppression.

11. A method for preparing a compound of formula I according to claim 1, by please solution synthesis, said method comprising the steps of:
   a) coupling the C-terminal amine substituent of said compound to the carboxylic acid function of Boc-Tic-OH to form a protected Tic amide derivative;
   b) deprotecting the product of step a) by treating said product with acid to form a deprotected Tic amide derivative;
   c) coupling a Boc-protected, N-terminal tyrosine or tyrosine analog to the amino group of said deprotected tic amide derivative; and
   d) deprotecting the product of step c).

12. The method of claim 11, wherein the coupling steps of said method are performed by the mixed anhydride method.

13. A method for the preparation of the compound

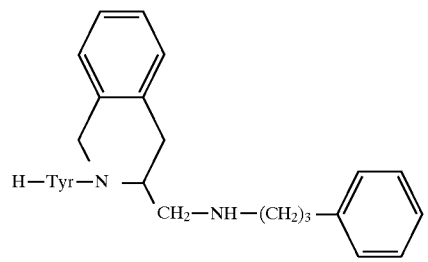

comprising the steps of:
   a) deprotecting Boc-Tic-3-(N-methoxy-N-methylamide) with acid;
   b) coupling Boc-Tyr(Boc)-OH to the product of step a);
   c) reducing the product of step b) with lithium aluminium hydride to obtain a dipeptide aldehyde;
   d) reacting said dipeptide aldehyde with a gamma phenylpropylamine;
   e) treating the product of step d) with sodium cyanoborohydride; and
   f) deprotecting the product of step e).

* * * * *